United States Patent [19]

Wiedrich et al.

[11] Patent Number: 4,584,420
[45] Date of Patent: Apr. 22, 1986

[54] METHOD FOR PRODUCING VINYL CHLORIDE

[75] Inventors: Charles R. Wiedrich, Barberton; John C. Crano, Akron, both of Ohio

[73] Assignee: PPG Industries, Inc., Pittsburgh, Pa.

[21] Appl. No.: 623,897

[22] Filed: Jun. 25, 1984

[51] Int. Cl.⁴ ............................................. C07C 17/34
[52] U.S. Cl. ................................................... 570/227
[58] Field of Search ........................................ 570/227

[56] References Cited

U.S. PATENT DOCUMENTS 3,222,407 12/1965 Leach et al. ......................... 260/656
3,655,787  4/1972 Wiley ............................... 260/656 R
3,860,595  1/1975 Kurtz et al. .......................... 570/227

FOREIGN PATENT DOCUMENTS 1210800  2/1966 Fed. Rep. of Germany .
40-27728 12/1965 Japan .
40-28779 12/1965 Japan .
1225210  3/1971 United Kingdom .

OTHER PUBLICATIONS

Ashmore et al., "Chlorine-Catalyzed Pyrolysis of 1,2-Dichloroethane", Part 1, *Journal of the Chemical Society, Faraday Trans.*, vol. 78 (1982), pp. 657–676; Part II, pp. 677–693.
*Chemical Abstracts*, vol. 64, 9591d (1966)–Abstracting Japanese 40-27728.
*Chemical Abstracts*, vol. 69, 43399d (1968)–Abstracting Japanese 42-19813.

*Primary Examiner*—Charles F. Warren
*Assistant Examiner*—Joseph A. Boska
*Attorney, Agent, or Firm*—George D. Morris

[57] ABSTRACT

Compound represented by the formula

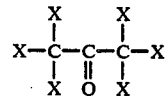

wherein each X is independently chloro or bromo is employed as a pyrolysis promoter in the pyrolysis of 1,2-dichloroethane to vinyl chloride.

10 Claims, No Drawings

METHOD FOR PRODUCING VINYL CHLORIDE

It is well known that vinyl chloride can be produced by the pyrolysis of 1,2-dichloroethane, also known as ethylene dichloride. See, for example, U.S. Pat. No. 3,655,787, the entire disclosure of which is incorporated herein by reference. Various materials have been added in small amounts to promote the pyrolysis reaction. There are, however, problems associated with many of the previously used promoters. For example, when molecular chlorine is added to the 1,2-dichloroethane feed before entering the pyrolysis furnace, the concentration must be fairly high, on the order of about 1000 parts per million parts of mixture by weight (ppm), in order to be reasonably effective as a promoter. Unless the furnace tubes are constructed of expensive corrosion resistant materials, the high chlorine content in the feed can lead to severe tube corrosion, carburization, and ultimately, tube failure. Reduced concentrations of molecular chlorine, on the order of about 100 ppm, while less corrosive to the furnace tubes, are reasonably effective only if the point or points of addition are within the pyrolysis furnace itself. Implementation of this method of addition in existing furnaces would require considerable capital expenditures for structural modifications. As another example, carbon tetrachloride has been used as a pyrolysis promoter, but increased carbon formation during the pyrolysis reaction has been attributed to its use.

The present invention is based on the discovery that perhalogenated acetone is effective as a pyrolysis promoter. Accordingly, in a process wherein 1,2-dichloroethane is pyrolyzed in a pyrolysis zone to produce vinyl chloride, the invention is the improvement comprising conducting the pyrolysis in the presence of a pyrolysis-promoting amount of promoter represented by the formula

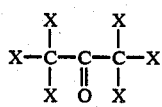

(I)

wherein each X in the promoter is independently chloro or bromo.

The promoter may be a single compound within the class represented by Formula I, or it may be a mixture of such compounds. Ordinarily, a single compound of the class is employed.

Although the various halo groups in the promoter molecule may be the same or different, it is preferred they be the same. It is especially preferred that each X in the promoter be chloro.

The preferred promoters are hexachloroacetone and hexabromoacetone. Hexachloroacetone is particularly preferred.

A pyrolysis-promoting amount of promoter is an amount of promoter which results in an increase in the yield of vinyl chloride based on 1,2-dichloroethane, as compared with the yield of vinyl chloride produced in the absence of the promoter under otherwise substantially identical conditions. The pyrolysis-promoting amount of promoter employed may vary widely. Usually, however, the promoter and the 1,2-dichloroethane are introduced to the pyrolysis zone at a weight ratio of promoter to 1,2-dichloroethane in the range of from about 0.00001:1 to about 0.01:1. Typically, the weight ratio is in the range of from about 0.0001:1 to about 0.001:1. From about 0.0002:1 to about 0.0008:1 is preferred.

The promoter and the 1,2-dichloroethane may be introduced to the pyrolysis zone as separate streams, but preferably they are admixed and the resulting mixture is introduced to the pyrolysis zone. When introduced separately, either or both of the materials may be introduced as either vapor, liquid or a mixture of vapor and liquid, but it is preferred that both be introduced as vapor. Each material may be introduced to the pyrolysis zone at one or more points. When a mixture of promoter and 1,2-dichloroethane is introduced to the pyrolysis zone, the mixture may be introduced as vapor, as liquid or as a mixture of vapor and liquid. It is preferred that the mixture be introduced as vapor. The mixture may be introduced to the pyrolysis zone at one or more points.

The pyrolysis is conducted in the vapor phase. While it may be conducted continuously, semicontinuously, batchwise, or semibatchwise, it is usually conducted continuously.

The temperatures at which the pyrolysis is conducted may vary widely, but ordinarily they are in the range of from about 350° C. to about 650° C. Preferably, the temperatures are in the range of from about 400° C. to about 550° C.

The pressures at which the pyrolysis is conducted are similarly susceptible to wide variation. While the pyrolysis may be conducted at ambient atmospheric pressure or below ambient atmospheric pressure, it is ordinarily conducted at pressures above ambient atmospheric pressure. Typically, the pressures are in the range of from about 80 to about 2000 kilopascals, gauge. Often it is in the range of from about 300 to about 1500 kilopascals, gauge. From about 700 to about 1100 kilopascals, gauge is preferred.

Likewise, the residence time of the reaction mixture in the pyrolysis zone may be widely varied. Generally the residence time is in the range of from about 0.1 to about 30 seconds. Often it is in the range of from about 0.5 to about 20 seconds. From about 1 to about 10 seconds is preferred.

Following pyrolysis, the vinyl chloride may be recovered from the reaction mixture by any of the various techniques known to the art. Quenching, fractional distillation, vaporization, and condensation are techniques which are frequently employed.

Purified vinyl chloride has a multitude of uses, but principally it is used as a monomer for producing homopolymers and interpolymers.

In the illustrative examples which follow, all parts are parts by weight and all percentages are percentages by weight unless otherwise specified.

EXAMPLE I

A reactor was fabricated by bending, a 1.22 meter length of borosilicate glass tubing 9 millimeters in external diameter into the shape of the letter "U". About 7 grams of borosilicate glass beads were placed in the bottom of the reactor. Into each leg of the reactor was placed a metal coupon. Each coupon was a strip of Inconel 600 nickel alloy 85 millimeters in length and weighing about 4 grams. The coupons had been prepared by cutting segments of Inconel 600 nickel alloy tubing in half lengthwise, filing the rough edges, and washing with water and then with acetone. Handling all the washed coupons was done with forceps to avoid fingerprints.

A graduated reservoir was connected via a metering pump to the inlet leg of the reactor. The outlet leg of the reactor was connected to one arm of a mixing tee. A source of nitrogen was connected via a metering valve and rotameter to the base of the mixing tee. The remaining arm of the mixing tee was connected to the inlet of a 110 milliliter sample bulb fitted with a rubber septum. The outlet from the sample bulb was connected to the gas inlet of a one meter water-scrubbing tower fabricated from a Vigreux column. Gas issuing from the gas outlet of the water-scrubbing tower was vented. Connections were made using poly(tetrafluoroethylene) tubing. The reactor containing the beads and coupons was placed in a bed of alumina particles which was fluidized by air and which could be heated by electrical heating elements at the base of the fluidized bed. The reactor was positioned so that the reactor volume available for gas flow below the surface of the fluidized bed was approximately 20 milliliters. A thermocouple was also placed in the fluidized bed.

A series of runs was conducted in which each run was divided into two phases. During the first phase, data were generated from which the yield of vinyl chloride could be calculated. During the second phase, data were generated from which the quantity of carbon that had accumulated in the reactor during the first phase could be calculated.

In the first phase, the reactor containing the beads and coupons was flushed with nitrogen prior to heating the fluidized bed. The fluidized bed was then heated to operating temperature and 1,2-dichloroethane, with or without a pyrolysis promoter as the case may be, was placed in the reservoir. The metering pump was turned on and the delivery rate was adjusted such that the 1,2-dichloroethane, upon vaporization and if unreacted, would have a residence time in that portion of the reactor below the surface of the fluidized bed at the operating temperature and an absolute pressure of one atmosphere, of about 4 seconds. The effluent from the reactor was diluted with dry nitrogen to insure a homogeneous vapor phase prior to entering the sample bulb. After passing through the sample bulb, the diluted effluent was contacted with cascading water in the water-scrubbing tower for hydrogen chloride removal and the remaining gases were vented. The duration of the first phase of each run was in the range of from 28 to 30 hours, during which time approximately ten samples were collected through the septum using a needle and syringe. The samples were analyzed and the yields of vinyl chloride based on 1,2-dichloroethane were calculated. These values were averaged and the standard deviation computed.

In the second phase of each run, the line from the reservoir to the reactor was replaced by a line from the outlet of a tee. A source of nitrogen was connected via a metering valve and rotameter to one inlet of the tee and a source of oxygen was connected via a metering valve and rotameter to the other inlet of the tee. The line from the sample bulb was detached from the water-scrubbing tower and connected to the first of three bulbs connected in series. The first bulb contained magnesium perchlorate while the second and third bulbs each contained a mixture of sodium hydroxide-coated silica (Ascarite II; Arthur H. Thomas Co.) and magnesium perchlorate. The purpose of the third bulb was to prevent back-diffusion of carbon dioxide and water vapor from the atmosphere which might adversely affect the results. After accurately weighing the second bulb, it was replaced in the line. A slow flow of nitrogen was introduced to the reactor to flush out any volatile organic materials. The slow flow of nitrogen was then replaced by a flow of oxygen at approximately 75 milliliters per minute (20° C., 1 atmosphere absolute). The temperature of the fluidized bed was brought to 500° C. and held at this temperature for about 20 minutes. During this time, the portions of the reactor above the level of the fluidized bed were carefully heated with a glass-blowing torch to burn off the remaining carbon film. The second bulb was weighed again and the weight difference due to carbon dioxide absorption was used to calculate the amount of carbon formed during the first phase of the run (weight carbon = weight gain $\times$ 0.273).

For each run, a new U-tube reactor, new beads, and new coupons were used. Feed solutions were prepared by dissolving the appropriate quantity of promoter in 1,2-dichloroethane. When duplicate runs were performed, the results were averaged and standard deviations computed.

The results showing the effect of hexachloroacetone (HCA) and molecular chlorine ($Cl_2$) as pyrolysis promoters are shown in Table 1. Other terms are related to their abbreviations as follows: vinyl chloride (VCl), mg (milligrams), parts per million parts by weight (ppm), and parts per million parts of vinyl chloride formed by weight (ppm/VCl).

TABLE 1

| Bed Temperature °C. | Additive Identity | ppm | VCl Yield, percent | Carbon Formation mg | ppm/VCl |
|---|---|---|---|---|---|
| 460 | None | — | 9 ± 4 | 6.4 | 145 |
| 460 | HCA | 300 | 45 ± 2 | 11.5 | 48 |
| 460 | $Cl_2$ | 100 | 40 ± 2 | 11.7 | 55 |
| 500 | None | — | 36 ± 5 | 15.3 ± 3.0 | 81 ± 9 |
| 500 | HCA | 300 | 63 ± 1 | 22.4 | 70 |
| 500 | $Cl_2$ | 100 | 56 ± 6 | 20.9 | 75 |

EXAMPLE II

A graduated reservoir was connected via a valve and metering pump to one arm of a tee. A source of nitrogen was connected via a metering valve and rotameter to the other arm of the tee. The base of the tee was connected to the inlet of a vaporizer/preheater. The vaporizer/preheater was about 0.81 meter long and was constructed of Inconel 600 nickel alloy tubing 9.525 millimeters in external diameter. The vaporizer/preheater was wrapped with high temperature electrical heating tape controlled by a Variac autotransformer. The entire assembly was insulated with glass fiber pipe insulation 2.54 centimeters thick. The outlet of the vaporizer/preheater was connected to the inlet of the reactor. The reactor was a coil of Incoloy 800 tubing about 4.839 meters long which was immersed in an electrically heated bed of air-fluidized alumina particles. The first 0.241 meter and the last 0.267 meter of the tubing was 9.525 millimeters in external diameter and had a wall thickness of 0.889 millimeter. The intermediate 4.331 meters of the tubing was 6.35 millimeters in external diameter and had a wall thickness of 0.889 millimeter. The outlet of the reactor was connected to a carbon dropout chamber 0.3048 meter long constructed of Type 316 stainless steel tubing 19.05 millimeters in external diameter and having a wall thickness of 1.2446 millimeter. The carbon dropout chamber contained glass fiber wool and was traced with electrical heating in Table 2. The abbreviations are as indicated in Example I.

TABLE 2

| Additive | | Experiment Duration, | VCl Yield, | By-Product Formation, ppm/VCl | | |
|---|---|---|---|---|---|---|
| Identity | ppm | hours | percent | Acetylene | Chloroprene | Butadiene |
| None | — | 7.43 | 43.37 ± 2.61 | 1035 ± 125 | 1079 ± 69 | 7.3 ± 0.3 |
| HCA | 300 | 3.37 | 51.14 ± 2.22 | 1175 | 1169 | 7.6 |
| HCA | 600 | 5.63 | 58.23 ± 1.13 | 1653 ± 186 | 1305 ± 188 | 3.6 ± 0.6 |
| None | — | 3.32 | 40.73 ± 0.91 | 1027 ± 113 | 854 ± 166 | 4.1 | tape controlled by a Variac autotransformer. The unit was insulated with glass fiber insulation. The outlet from the carbon dropout chamber was connected to a pressure control system. The process line of the pressure control system was traced with electrical heating tape controlled by a Variac autotransformer and was insulated with glass fiber insulation. The outlet from the control valve of the pressure control system was connected to one arm of a tee. The other arm of the tee was connected in series to a condenser cooled by a 1:1 mixture of methanol and water entering at about −15° C., a water-scrubbing tower, a wet test meter, an incinerator and a vent. The base of the tee was connected in series to a metering valve, a mass flow transducer a mixing tee where nitrogen from a metering valve and rotameter was introduced. The outlet from the mixing tee was connected to the arm of another tee. The other arm of this tee was fitted with a septum through which samples could be taken using a needle and syringe. The base of the tee was connected to a vent. The entire apparatus was provided throughout with thermocouples, pressure gauges, transducers, controllers, indicators, valves, a pressure relief valve, and other equipment conventionally associated with reactors of this general type.

The various parts of the apparatus were brought to operating temperatures while nitrogen was passed through the system. Feed material was placed in the reservoir. The flow of nitrogen to the first tee was discontinued and the metering pump was turned on. The delivery rate of the metering pump was adjusted to deliver 7.5±0.4 moles of 1,2-dichloroethane per hour. The pressure at the reactor inlet was held at about 862 kilopascals, gauge. The maximum temperature of the vaporizer/preheater was about 380° C. while the temperature of the fluidized bed was about 460° C. Samples were taken throughout each experiment. The solutions of hexachloroacetone and 1,2-dichloroethane were prepared by dissolving the appropriate quantity of hexachloroacetone in 1,2-dichloroethane. Changes of feed material in the reservoir were done so that flow rate, pressure, and temperatures were not disrupted.

For each experiment, where a plurality of results were obtained, they were averaged and the standard deviations computed. The results showing the effect of hexachloroacetone as a pyrolysis promoter are shown Although the present invention has been described with reference to specific details of certain embodiments thereof, it is not intended that such details should be regarded as limitations upon the scope of the invention except insofar as they are included in the accompanying claims.

We claim:

1. In a process wherein 1,2-dichloroethane is pyrolyzed in a pyrolysis zone to produce vinyl chloride, the improvement comprising conducting the pyrolysis in the presence of a pyrolysis-promoting amount of promoter represented by the formula

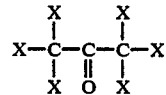

wherein each X in said promoter is independently chloro or bromo.

2. The process of claim 1 wherein each X in said promoter is the same.

3. The process of claim 1 wherein said promoter is hexachloroacetone.

4. The process of claim 1 wherein said promoter and said 1,2-dichloroethane are introduced to said pyrolysis zone at a weight ratio of promoter to 1,2-dichloroethane in the range of from about 0.00001:1 to about 0.01:1.

5. The process of claim 1 wherein said promoter and said 1,2-dichloroethane are admixed and the resulting mixture is introduced to said pyrolysis zone.

6. The process of claim 5 wherein the weight ratio of said promoter to said 1,2-dichloroethane in said mixture is in the range of from about 0.00001:1 to about 0.01:1.

7. The method of claim 1 wherein the pyrolysis is conducted at temperatures in the range of from about 350° C. to about 650° C.

8. The method of claim 1 wherein the pyrolysis is conducted at pressures above ambient atmospheric pressure.

9. The method of claim 8 wherein said pressures are in the range of from about 80 to about 2000 kilopascals, gauge.

10. The method of claim 1 wherein the residence time of the reaction mixture in said pyrolysis zone is in the range of from about 0.1 to about 30 seconds.

* * * * *